United States Patent [19]
Hager et al.

[11] Patent Number: 5,741,517
[45] Date of Patent: *Apr. 21, 1998

[54] WATER-CONTAINING LIPOSOME SYSTEM

[75] Inventors: Jörg Hager, Köln; Manfred Dürr, Pulheim-Dansweiler; Ernst Lünebach, Erftstadt-Lechenich, all of Germany

[73] Assignee: A. Nattermann & Cie GmbH, Cologne, Germany

[*] Notice: The term of this patent shall not extend beyond the expiration date of Pat. No. 5,556,637.

[21] Appl. No.: 650,736

[22] Filed: May 20, 1996

Related U.S. Application Data

[63] Continuation of Ser. No. 371,380, Jan. 11, 1995, Pat. No. 5,556,637, which is a continuation of Ser. No. 29,977, Mar. 12, 1993, abandoned, which is a continuation of Ser. No. 738,837, Aug. 1, 1991, abandoned.

[30] Foreign Application Priority Data

| Aug. 6, 1990 | [DE] | Germany | 40 24 886.0 |
| Mar. 19, 1991 | [DE] | Germany | 41 08 902.2 |
| Jul. 10, 1991 | [DE] | Germany | 41 22 744.1 |

[51] Int. Cl.$^6$ ............................ A61K 9/127
[52] U.S. Cl. .................... 424/450; 428/402.2
[58] Field of Search ............ 424/450; 428/402.2; 436/829

[56] References Cited

U.S. PATENT DOCUMENTS

| 4,241,046 | 12/1980 | Papahadjopoulos et al. | 424/19 |
| 4,348,384 | 9/1982 | Horikoshi et al. | 424/101 |
| 4,668,638 | 5/1987 | Janoff | 424/450 |
| 4,744,989 | 5/1988 | Payne et al. | 424/490 |
| 4,776,991 | 10/1988 | Farmer et al. | 264/4.3 |
| 4,781,871 | 11/1988 | West | 264/4.3 |
| 4,814,270 | 3/1989 | Piran | 436/528 |
| 4,828,837 | 5/1989 | Uster | 424/450 |
| 4,839,111 | 6/1989 | Huang | 264/4.6 |
| 4,946,683 | 8/1990 | Forssen | 424/422 |

FOREIGN PATENT DOCUMENTS

| 0 274 174 | 7/1988 | European Pat. Off. |
| 0 315 467 | 5/1989 | European Pat. Off. |
| 0 331 635 | 9/1989 | European Pat. Off. |
| 3 016 976 | 11/1980 | Germany |
| 3 301 951 | 7/1984 | Germany |
| 2 002 319 | 2/1979 | United Kingdom |
| 8 806 443 | 9/1988 | WIPO |

OTHER PUBLICATIONS

J. Roding, "Natipide II: New easy liposome system", Seifen–Ole–Fette–Washse–118, No. 14, 1990, pp. 509–516, 560.
Deamer. In Liposomes, p. 27, 1983.
Higgins, J. Pharmacol. 39, 577 (1987).

*Primary Examiner*—Gollamudi S. Kishore
*Attorney, Agent, or Firm*—Meltzer, Lippe, Goldstein, Wolf & Schlissel, P.C.

[57] ABSTRACT

An aqueous liposome system which contains at least one phospholipid and selectively a non-toxic organic solvent. In addition to the at least one phospholipid the liposome system contains at least one phospholipidic charge carrier.

26 Claims, No Drawings

WATER-CONTAINING LIPOSOME SYSTEM

This is a continuation of application Ser. No. 08/371,380, filed Jan. 11, 1995, now U.S. Pat. No. 5,556,637, which is a continuation of application Ser. No. 08/029,977, filed Mar. 12, 1993, now abandoned, which is a continuation of application Ser. No. 07/738,837, filed Aug. 1, 1991, now abandoned.

The present invention is directed to a water-containing liposome system and to a method of producing such a liposome system.

Phospholipidic liposome systems are known for different kinds of applications. So, these systems are for example used in the cosmetic field or for the production of pharmaceutical products. The respective active ingredients are encapsulated in spheres (vesicles) designated liposomes. These liposomes preferably contain an aqueous phase in their interior in which the respective active ingredient is correspondingly dissolved, dispersed or emulsified. The liposomes are confined towards the outside by a lipid double membrane.

EP A 03 09 519 and EP A 03 15 467 describe liposome systems which encapsulate the active ingredient pentamidin and which are used as pharmaceutical products.

The known liposome systems have often the disadvantage that they have the tendency to form undesired sediments even after a short time.

The present invention is based on the problem to provide a water-containing phospholipidic liposome system which has an especially high stability and thus does not tend to the formation of sediments.

The inventive water-containing liposome system has at least one phospholipidic charge carrier in addition to the at least one phospholipid.

The inventive liposome system has a number of advantages. So, it could be observed that the inventive liposome system, even at an extremely long storage time of several months up to years, did not show any tendency to form sediments or deposits, on the walls of the vessels. Furthermore, the inventive liposome system has a high transparency and is not dull or opaque which is the case with the known liposome systems. This has the result that an inspection with regard to the presence of foreign particles can be carried out without any difficulties with the inventive liposome system since it is only necessary for this to inspect the corresponding liposome dispersions by looking through the same. Moreover, it is adapted to be filtrated in a sterile manner so that the inventive liposome systems are especially suited for a pharmaceutical or cosmetic application.

The above-described advantageous effects of the inventive liposome system are attributed to the fact that obviously the presence of the negative phospholipidic charge carrier has the result of a synergistic effect.

An embodiment of the inventive liposome system containing as phospholipidic charge carrier at least one salt, preferably a sodium salt and/or an ammonium salt, of phosphatidylglycerol and/or of the derivatives thereof has especially good results with respect to the above-cited advantages. Preferably, the salt is the corresponding salt of dimyristoylphosphatidylglycerol and/or dipalmitoylphosphatidylglycerol.

On principle, according to the inventive liposome system the phosphatidylglycerol, which is present as a corresponding salt and thus forms the preferred negative phospholipidic charge carrier according to the above-described embodiments, can be isolated from any natural substance, as for example from oil seeds, rape, sun flowers etc., and can be used correspondingly, possibly after a purification. However, it is especially advantageous if the above-cited salts of the phosphatidylglycerol or the corresponding derivatives are isolated from soya beans so that a soya phosphatidylglycerol alkaline salt, especially sodium salt or potassium salt, or a soya phosphatidylglycerol derivative alkaline salt, preferably sodium salt or potassium salt, is preferably used as negative charge carrier in the inventive liposome system.

With regard to the mass ratio of the at least one phospholipid and the at least one negative phospholipidic charge carrier it is to be stated that this mass ratio varies between 50:1 to 400:1, preferably between 100:1 to 200:1. It could be observed that already the above-cited small amounts of the negative charge carrier are sufficient to give the above-cited stability during storage and a high transparency to the phospholipidic liposome system produced herefrom. An embodiment of the inventive liposome system which contains phosphatidylcholine as phospholipid has an especially long durability as well as an especially high distribution of the liposomes. Especially in the case if the phosphatidylcholine is ultra-pure phosphatidylcholine, i. e. phosphatidylcholine containing less than about 10% by weight impurities, a liposome system produced herefrom preferably containing the above-described soya phosphatidylglycerol sodium salt as negative phospholipidic charge carrier has the above-described advantageous characteristics. Furthermore, such a specific liposome system can be homogeneously comminuted to a desired mean particle diameter of between 50 nm and 180 nm, preferably between 70 nm and 130 nm, by high-pressure split homogenisation or ultrasonic treatment with essentially less effort and thus in about half of the time. Such a specific liposome system can also be filtrated in a sterile manner without any problems. For this, preferably 0.2 µm filters are used.

As regards the phospholipid concentration of the inventive liposome system, it is to be stated that the same varies between 0.5% by weight and 20% by weight.

As already described above, the inventive liposome system can be used not only for pharmaceutical but also for cosmetic purposes.

If the inventive liposome system is used for pharmaceutical purposes, two possibilities exist:

According to the first possibility the inventive liposome system is used as a blank liposome system, i.e. the liposome system as such is already pharmaceutically active. With regard to such a system it could be observed that the same can be used in an excellent manner for the treatment of atherosclerosis (arteriosclerosis), increased blood fat values as well as hepatopathies of any genesis. Such a system contains preferably water, possibly alcohol and between 5% by weight and 15% by weight of a mixture of phosphatidylcholine and negative charge carrier in the above-cited mass ratio. Such a pharmaceutical product is especially injected when applied.

According to the second possibility an active ingredient is encapsulated into the inventive liposome system. Such an encapsulated active ingredient has an improved therapeutical effect compared with the known product without negatively influencing the aim of the medical treatment. This effect is attributed to the fact that the active ingredients encapsulated into the liposome system are delivered especially uniformly during a longer period of time during the therapeutical treatment so that undesired secondary effects do not occur or will be at least substantially reduced.

The selection of the respective active ingredient depends on the respective field of application. So, for example pentamidin, pentamidin salts, especially pentamidin isethionate, and/or pentamidin derivatives can be dissolved and/or encapsulated in the inventive liposome system so that such a pharmaceutical product is preferably used for the parenteral and especially pulmonary treatment of pneumocystis-carinii-pneumonia (PcP), of the African sleeping sickness or of kala-azar.

However, it is especially advantageous if the above-cited active ingredient is not used from the beginning of the production of the liposome system but is added only at a point of time immediately prior to the application. This can be done by mixing an aqueous liposome system with the active ingredient as dry substance or at first dispersing a dried liposome system in water and subsequently mixing the same with the active ingredient. A pharmaceutical product produced in such a manner has a high transparency. In certain cases similar effects are attained by combining blank liposome preparations with the active ingredient without encapsulating the active ingredient into the liposome.

If the inventive liposome system contains Doxorubicin x HCl as active ingredient, it can be used as corresponding pharmaceutical product for the treatment of cancer diseases.

If the inventive liposome system is to be used for the treatment of virus diseases, especially virus diseases of the skin, it is preferred to encapsulate a corresponding virucide active ingredient, preferably rosemary acid or dextrane sulfate.

Furthermore, also the known active ingredients for the treatment of cancer, AIDS, liver diseases or virus diseases can be encapsulated or agglomerated in the inventive liposome system.

Moreover, the invention is directed to a method of producing the above-described liposome system.

The inventive method of producing the inventive liposome system is based on the fundamental cognition that at first the used phospholipid, especially the above-described phosphatidylcholine or ultra-pure phosphatidylcholine, together with the phospholipidic charge carrier, especially the soya phosphatidylglycerol sodium salt, is dissolved or dispersed in an organic solvent. Thereafter, the solution or dispersion is concentrated, and a corresponding amount of water is added in order to form the corresponding liposome system.

Preferably, ethanol, propanol 1 and/or propanol 2 are used as solvent in the above-described inventive method.

The solution or dispersion produced in the beginning is concentrated to different residual volumes dependent on the used non-toxic organic solvent and its ability to be mixed or its compatibility with water. If, for example, the above-cited alcohols are used as non-toxic organic solvents, it is preferred to concentrate the corresponding solution of the phospholipid with the negative phospholipidic charge carrier to a residual volume of between 3 vol. (volume) % and 30 vol. %, preferably of 5 vol. % to 10 vol. %. With such organic solvents which cannot be mixed with water it is recommended to concentrate until the dry condition.

In order to produce a liposome system with the inventive method which is characterized by especially uniform and adjusted mean liposome diameters, it is preferred to subject the resulting liposome system to a high-pressure split homogenisation or an ultrasonic treatment after the addition of water. Preferably, these treatments are carried out until the liposomes formed thereby have a mean diameter between 50 nm and 180 nm.

In addition, hereafter the liposome system treated in such a manner can be filtrated in a sterile manner by means of a 0.2 μm filter.

Then, the produced liposome systems can be either directly filled into corresponding ampoules in a condition ready for application or can be carefully dried, especially freeze dried, after the addition of suitable assisting substances, especially carbon hydrates, so that a powder-like liposome system develops which, by means of the addition of a suitable amount of water, again forms the desired vesicles which are ready for application without making necessary extensive measures for agitation or mixing.

Again, two possibilities exist in order to produce the embodiment of the inventive liposome system having one of the above-cited active ingredients.

According to the first possibility the active ingredient together with the phospholipid and the phospholipidic charge carrier is added to the organic solvent directly at the beginning of the inventive method. According to a variant of this method the used phospholipid is loaded with the active ingredient dissolved, dispersed or emulsified in a non-aqueous solvent, and after carefully drying the phospholipid loaded in such a manner together with the phospholipidic charge carrier are dissolved in an organic solvent which is possibly different from the first solvent. Thereafter, the organic solvent, as described above, is concentrated, and hereafter the water is added so that the active ingredient-liposome-system is formed wherein the active ingredient can be encapsulated. This variant of the method is especially preferred for such cases according to which the active ingredient is stable with regard to its storage.

According to the second possibility, which is preferred especially if the active ingredient cannot be dissolved in the organic solvent used at first but can be better dissolved in water, at first the aqueous liposome system is produced in the above-described manner wherein thereafter the active ingredient is added together with the water.

A modification of the above-described method, which is especially used if the active ingredient has only a limited durability, is based on powder-like dried liposome system. According to this modification the active ingredient is added during the redispersing step together with the used water so that the active ingredient comes into contact with the liposome system only immediately prior to the use of such a product.

In order to exclude undesired secondary effects the inventive method is preferably carried out under protection gas (inert gas).

Preferred embodiments of the inventive method are indicated in the subclaims.

In the following the inventive method is discussed in detail by means of examples.

EXAMPLE 1

Production of a Blank Liposome System 99.5 g of ultra-pure phosphatidylcholine, i.e. less than 10% by weight impurities, and 0.5 g soya phosphatidylglycerol sodium salt (PG) were dissolved in 500 ml ethanol DAB (German pharmacopeia 9) and subsequently dried under vacuum. The obtained phospholipid mixture was dispersed in water for injection purposes ad 1000 ml under agitation and inert gas and thereafter was brought to a mean particle diameter of <100 nm by means of a high-pressure split homogenisator in five cycles. The resulting liposome system was thereafter filtrated through a 0.2 μm filter under sterile conditions and was filled into 10.0 ml ampoules under a gas atmosphere. The phosphatidylcholine/soya-PG-sodium system liposome system produced according to example 1 had the following characteristics:

| | |
|---|---|
| phospholipid content: | 10% (m/V) |
| appearance: | transparent, slightly opalescent liquid |
| pH: | 6.1 |
| viscosity: | 2.6 mPa · s |
| osmotic pressure: | 0.49 (% NaCl) |
| transmission (660 nm): | 75% |
| mean particle diameter (laser light dispersion): | 75 nm |
| sterility: | corresponds to examination for sterility, DAB 9 (German pharmacopeia) |
| endotoxin content (Limulustest): | corresponds to requirements of DAB 9 |
| electron microscopic characterization (cryofixation): | 40–100 nm unilamellar liposomes, seldom bilamellar liposomes |

On account of its composition this product can be used in the following fields of application: atherosclerosis, increased blood fat values, hepatopathies of any genesis.

EXAMPLE 2

500 g of phospholipid mixture consisting of 497.5 g ultra-pure phosphatidylcholine, i. e. less than 10% by weight impurities, and of 2.5 g soya-PG-sodium salt produced according to example 1 were dispersed in 6.5 l water for injection purposes under agitation and inert gas. Thereafter, it was filled up with water for injection purposes to 8.0 l. In a separate vessel 2 kg of maltose were dissolved in 1.5 l water for injection purposes under heating to 70° C. The phospholipid system was brought to a mean particle diameter of 56 nm by several cycles in a high-pressure split homogenisator (APV Gaulin, type LAB 60), was mixed with the maltose solution under agitation and inert gas, was filled up with water for injection purposes to 10.0 l, was sterile filtrated, was filled under aseptic conditions and was freeze dried. The lyophilisate formed after the freeze drying had the following characteristics:

| | |
|---|---|
| appearance: | crystalline, slight yellow dry powder |
| content of residual moisture according to Karl Fischer: | <0.7% |
| content of phospholipids: | 500 mg/Vial |
| sterility: | corresponds to examination for sterility according to DAB 9 |
| endotoxin content (Limulustest): | corresponds to requirements of DAB 9 |

After redispersion of the lyophilisate with 8.3 ml water for injection purposes a liposome system with the following characteristics was obtained:

| | |
|---|---|
| appearance: | transparent, slightly opalescent liquid |
| pH: | 6.5 |
| viscosity: | 2.7 mPa · s |
| transmission (660 nm): | 72% |
| mean particle diameter (laser light dispersion method): | 60 nm |

The phospholipid liposome system produced according to example 1 and the lyophilisate produced according to example 2 can be used for the following purposes of application: atherosclerosis, increased blood fat values, hepatopathies of any genesis. The lyophilisate produced according to example 2 has the advantage of an increased stability compared with the aqueous liposome system produced according to example 1.

The phospholipid mixture produced according to example 1 and consisting of phosphatidylcholine and soya-PG-sodium salt can be used not only for the production of unloaded, sterile filtratable phosphatidylcholine liposome systems examples 1+2) but also for the production of loaded sterile liposome systems (examples 3–5).

EXAMPLE 3

10 g of the inventive phospholipid mixture were dissolved together with 0.1 g propidiumiodide ((DNA-marker) in ethanol according to example 1 and dispersed in 100 ml water for injection purposes after drying under vacuum, inert gas and cooling. Thereafter, an ultrasonic treatment was carried out, also under inert gas and cooling, until a mean particle diameter of the liposomes of 80 nm (laser light dispersion) was attained. Then, the liposome system was sterile filtrated through a 0.2 μm filter, and a half thereof was filled into brown 1.0 ml ampullas under inert gas. The proportion of liposomal-bound propidiumiodide was determined in the sterile liposome system loaded with propidiumiodide by means of a dialysis method (Dianorm® apparatus, cellulosetriacetate membrane NMGT 20000). According to this, the liposomal-bound propidiumiodide proportion was 29%. In the second half which was sterile filtrated the proportion of non-liposomal-bound propidiumiodide was separated by means of ultrafiltration through a cellulosetriacetate membrane NMGT 20000. The liposome dispersion was once again sterile filtrated through 0.2 μm and for 1.0 ml filled into brown ampullas under inert gas. The obtained liposome dispersion had the following characteristics:

| | |
|---|---|
| phospholipid content: | 100 mg/ml |
| propidiumiodide content: | 0.285 mg/ml |
| pH: | 7.2 |
| viscosity: | 1.7 mPa · s |
| mean particle diameter (laser light dispersion): | 129 nm |

EXAMPLE 4

18.4 g of the phospholipid mixture described in example 1 together with 0.2 g quinoline yellow were dissolved in ethanol, dried under vacuum, dispersed with water for injection purposes ad 200 ml and thereafter subjected to an ultrasonic treatment under cooling. The obtained liposome system was thereafter sterile filtrated and filled into injection bottles for 5.0 ml under aseptic conditions. The sterile filtrated liposome dispersion had the following characteristics:

| | |
|---|---|
| appearance: | transparent, opalescent yellow liquid |
| pH: | 6.4 |
| mean particle diameter (laser light dispersion method): | 75 nm |
| transmission (660 nm): | 33% |
| sterility: | corresponds to examination for sterility, DAB 9 |
| quinoline yellow, liposomal-bound: | 1.38 mg/ml |
| quinoline yellow, non-liposomal-bound: | 3.2 mg/ml |

The non-liposomal-bound quinoline yellow proportion was separated for determining the proportion of liposomal-bound quinoline yellow by means of ultrafiltration through a cellulosetriacetate membrane NMGT 20000, and the proportion of quinoline yellow was photometrically determined in the liposome dispersion and in the filtrate.

The inventive phospholipid mixture transferred according to example 2 into a sterile dry powder is also suited for the extemporated (ready to use) production of liposomes loaded with active water-soluble substances.

EXAMPLE 5

A sterile dry powder corresponding to 500 mg phospholipid mixture described in example 1 and 2000 mg carrier substance were dispersed with 5.0 ml Doxorubicin HCl-solution (10.0 mg Doxorubicin HCl). The obtained liposome redispergate (6.8 ml) loaded with Doxorubicin HCl had a content of phospholipids of 73.5 mg/ml and a total content of Doxorubicin HCl of 0.735 mg/ml. The proportion of liposomal-bound Doxorubicin HCl was determined with 0.58 mg/ml and corresponds to an inclusion rate of about 78%.

The determination of the liposomal-bound Doxorubicin HCl proportion was carried out with the dialysis method by means of liposomates, amount 5.0 ml, duration 5 h.

EXAMPLE 6

Production of a Blank Liposome System 100 g of ultra-pure phosphatidylcholine, i. e. less than 10% by weight impurities, and 0.502 g soya phosphatidylglycerol sodium salt (PG) were dissolved in 500 ml ethanol DAB 9 and subsequently adjusted to a dry substance content of 92% by weight under vacuum. The obtained phospholipid mixture consisting of 91.54% by weight phosphatidylcholine, 6.46% by weight soya phosphatidylglycerol sodium salt, 6% by weight ethanol and 2% by weight water was dispersed in water for injection purposes ad 1000 ml under agitation and inert gas and thereafter brought to a mean particle diameter of <100 nm by means of high-pressure split homogenisator in five cycles. The obtained liposome system was thereafter filtrated through a 0.2 µm filter under sterile conditions and was filled into 10.0 ml ampoules under inert gas. The phosphatidylcholine/soya-PG-sodium-system liposome system produced according to example 6 has the following characteristics:

| phosphatidylcholine content | 10% (m/V) |
|---|---|
| appearance: | transparent, slightly opalescent liquid |
| pH: | 6.1 |
| viscosity: | 2.6 mPa · s |
| osmotic pressure: | 0.49 (% NaCl) |
| transmission (660 nm): | 75% |
| mean particle diameter (laser light dispersion): | 75 nm |
| sterility: | corresponds to examination for sterility, DAB 9 |
| endotoxin content (Limulustest): | corresponds to requirements of DAB 9 |

On account of its composition this product can be used in the following fields of application: atherosklerosis, increased blood fat values, hepatopathies of any genesis.

EXAMPLE 7

Production of a Blank Liposome System 100 g of ultra-pure phosphatidylcholine, i.e. less than 10% by weight impurities, and 0.502 g soya phosphatidylglycerol sodium salt (PG) were dissolved in 500 ml ethanol DAB 9 and thereafter adjusted to a dry substance content of 92% by weight under vacuum. The obtained phospholipid mixture consisting of 91.54% by weight phosphatidylcholine, 0.46% by weight soya phophatidylglycerol sodium salt, 6% by weight ethanol and 2% by weight water was dispersed in water for injection purposes ad 8333 ml under agitation and inert gas and thereafter brought to a mean particle diameter of <100 nm by means of a high-pressure split homogenisator at 500 bar in five cycles. The obtained liposome system was thereafter filtrated through a 0.2 µm filter under sterile conditions and filled into 10.0 ml ampoules under inert gas. The phosphatidylcholine/soya-PG-sodium-system liposome system produced according to example 7 had the following characteristics:

| phosphatidylcholine content: | 1.2% (m/V) |
|---|---|
| appearance: | transparent, slightly opalescent liquid |
| pH: | 6.19 |
| viscosity: | 1.4 mPa · s |
| transmission (660 nm): | 82% |
| mean particle diameter (laser light dispersion): | 58 nm |
| sterility: | corresponds to examination for sterility, DAB 9 |
| endotoxin content (Limulustest): | corresponds to requirements of DAB 9 |

We claim:

1. A liposome composition comprising at least one uncharged phospholipid, said uncharged phospholipid comprising at least 90% by weight of phosphatidylcholine, at least one negatively charged phospholipid, and water forming an aqueous phase for said liposome composition, wherein said negatively charged phospholipid is a salt of phosphatidylglycerol, wherein the mass ratio of the uncharged phospholipid to the charged phospholipid is in the range of about 50:1 to about 400:1, and the total phospholipid content of the liposome composition is between 0.50 and 20% by weight.

2. The liposome composition of claim 1 wherein the mass ratio of the phospholipid to the charged phospholipid is in the range of about 100:1 to about 200:1.

3. The liposome composition of claim 1 wherein said negatively charged phospholipid is a sodium or ammonium salt of a phosphatidylglycerol.

4. The liposome composition of claim 1 wherein said negatively charged phospholipid is a salt of dimyristoylphosphatidylglycerol or dipalmitoylphosphatidylglycerol.

5. The liposome composition of claim 1 wherein said negatively charged phospholipid is a salt of a soya phosphatidylglycerol.

6. The liposome composition of claim 1 wherein said phospholipid has less than 10% by weight impurities.

7. The liposome composition of claim 1 further comprising at least one pharmaceutically active substance.

8. The liposome composition of claim 7 wherein said pharmaceutically active substance is selected from the group consisting of doxorubicin.HCl, pentamidine, a pentamidine salt, rosemarinic acid, a salt of rosemarinic acid, and dextran sulfate.

9. The liposome composition of claim 1 further comprising an organic solvent present in said aqueous phase.

10. The liposome composition of claim 9 wherein said organic solvent is selected from the group consisting of ethanol, propanol-1, propanol-2, and mixtures thereof.

11. A composition suitable for forming liposomes, comprising at least one uncharged phospholipid, said uncharged phospholipid comprising at least 90% by weight of phosphatidylcholine, and at least one negatively charged phospholipid, wherein said negatively charged phospholipid is a salt of phosphatidylglycerol, wherein the mass ratio of the uncharged phospholipid to the charged phospholipid is in the range of about 50:1 to about 400:1, and the total phospholipid content of the composition is between 0.5 and 20% by weight, said liposomes being formed when water is added to said composition.

12. The composition of claim 11 wherein the mass ratio of the phospholipid to the charged phospholipid is in the range of about 100:1 to about 200:1.

13. The composition of claim 11 wherein said negatively charged phospholipid is a sodium or ammonium salt of a phosphatidylglycerol.

14. The composition of claim 11 wherein said negatively charged phospholipid is a sodium or ammonium salt of dimyristoylphosphatidylglycerol or dipalmitoylphosphatidylglycerol.

15. The composition of claim 11 wherein said negatively charged phospholipid is a salt of a soya phosphatidylglycerol.

16. The composition of claim 11 further comprising at least one pharmaceutically active substance.

17. The composition of claim 16 wherein said pharmaceutically active substance is selected from the group consisting of doxorubicin.HCl, pentamidine, a pentamidine salt, rosemarinic acid, a salt of rosemarinic acid, and dextran sulfate.

18. A composition suitable for forming liposomes, comprising at least one uncharged phospholipid, said uncharged phospholipid comprising at least 90% by weight of phosphatidylcholine, at least one negatively charged phospholipid, wherein said negatively charged phospholipid is a salt of phosphatidylglycerol, wherein the mass ratio of the uncharged phospholipid to the charged phospholipid is in the range of about 50:1 to about 400:1, and at least one organic solvent which is selected from the group consisting of ethanol, propanol-1, propanol-2, and mixtures thereof, and the total phospholipid content of the composition is between 0.5 and 20% by weight, said liposomes being formed when water is added to said composition.

19. The composition of claim 18 wherein the mass ratio of the phospholipid to the charged phospholipid is in the range of about 100:1 to about 200:1.

20. The composition of claim 18 wherein said negatively charged phospholipid is a sodium or ammonium salt of a phosphatidylglycerol.

21. The composition of claim 18 wherein said negatively charged phospholipid is a sodium or ammonium salt of a dimyristoylphosphatidylglycerol or dipalmitoylphosphatidylglycerol.

22. The composition of claim 18 wherein said negatively charged phospholipid is a salt of a soya phosphatidylglycerol.

23. The composition of claim 18 further comprising at least one pharmaceutically active substance.

24. The composition of claim 23 wherein said pharmaceutically active substance is selected form the group consisting of doxorubicin.HCl, pentamidine, a pentamidine salt, rosemarinic acid, a salt of rosemarinic acid, and dextran sulfate.

25. The composition of claim 18 wherein said composition contains said solvent in a concentration between 3% by volume and 30% by volume.

26. The composition of claim 18 wherein said composition contains said solvent in a concentration between 5% by volume and 10% by volume.

* * * * *